United States Patent [19]

Wright

[11] 4,191,187
[45] Mar. 4, 1980

[54] MEDICAL APPARATUS

[75] Inventor: Basil M. Wright, Rickmansworth, England

[73] Assignee: National Research Development Corporation, London, England

[21] Appl. No.: 884,545

[22] Filed: Mar. 8, 1978

[30] Foreign Application Priority Data

Mar. 9, 1977 [GB] United Kingdom ............... 09947/77

[51] Int. Cl.² .............................................. A61M 5/20
[52] U.S. Cl. ........................... 128/218 A; 128/DIG. 1
[58] Field of Search ........... 128/218 A, 218 R, 218 C, 128/215, 216, 234, DIG. 1, 2 R; 222/76, 333

[56] References Cited

U.S. PATENT DOCUMENTS

| 2,602,446 | 7/1952 | Glass et al. | 128/DIG. 1 |
| 3,701,345 | 10/1972 | Heilman et al. | 128/218 A |
| 3,812,843 | 5/1974 | Wootten et al. | 128/2 R |
| 3,858,581 | 1/1975 | Kamen | 128/218 A |

FOREIGN PATENT DOCUMENTS 2529636 2/1977 Fed. Rep. of Germany .... 128/DIG. 1

Primary Examiner—John D. Yasko
Attorney, Agent, or Firm—Cushman, Darby & Cushman

[57] ABSTRACT

Apparatus for driving a medical syringe plunger into its barrel at a variable controlled rate comprises an elongate support along which the syringe is secured, an electric motor, a transmission assembly drivably coupled with the motor to close the plunger into the barrel, a drive control for pulsing the motor to effect repeated constant incremental movements of the plunger through the transmission assembly, and a safety control operable to inhibit the drive control in response to continuous energization of the motor beyond a predetermined period. The safety control conveniently involves a capacitor charged by the motor pulses, and a latch activated by an "excess" charge on the capacitor relative to a normal situation.

10 Claims, 3 Drawing Figures

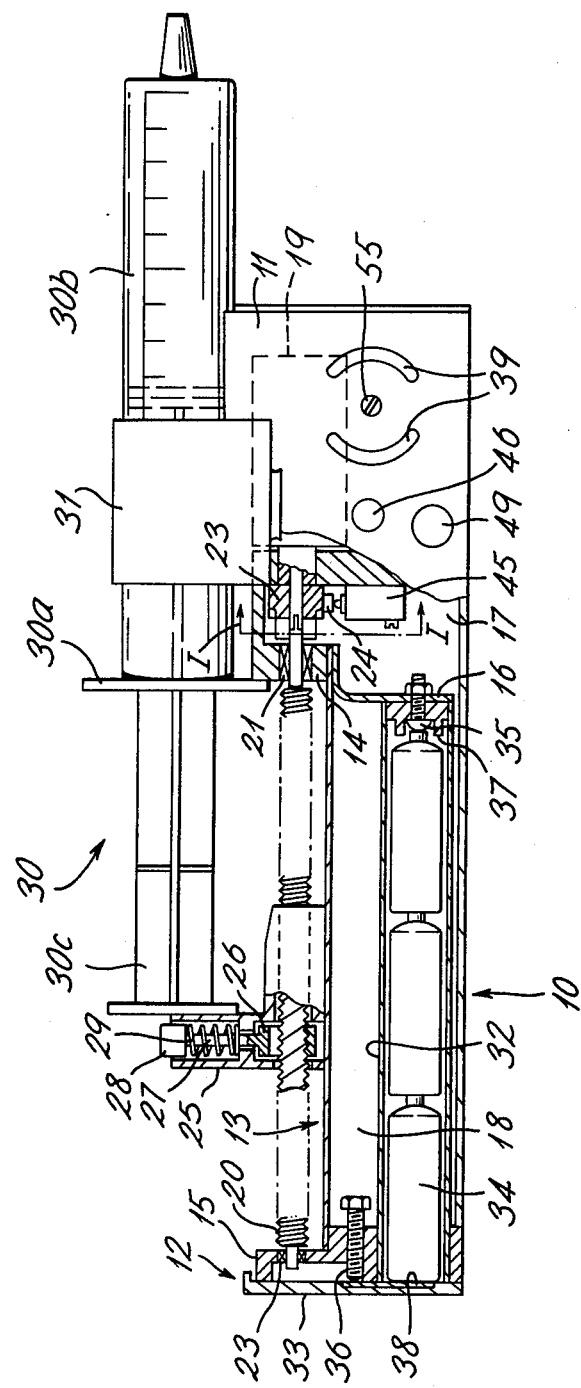
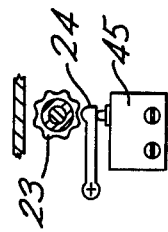
Fig. 1
Fig. 2

MEDICAL APPARATUS

This invention relates to medical apparatus and concerns, more particularly, syringe driving apparatus.

There is a growing appreciation of the benefits of drug administration in a substantially continuous manner by the use of a power-driven syringe applied by way of a cannula. Indeed, there have been proposals for apparatus to meet this purpose, but none of these proposals appears satisfactory for general purposes.

There are a number of factors in respect of which a motor-driven syringe apparatus can be unsatisfactory, such factors including the following:

(1) The apparatus should, of course, be safe and a facility should accordingly be provided to take account of hazardous malfunctions which may arise.

(2) The apparatus should, equally well, be reliable in terms of a dosage administered thereby being sufficiently accurate for the relevant clinical purposes.

(3) The apparatus should preferably be capable of administering dosages within a wide range in terms of quantity and period to afford a corresponding wide range of practical application.

(4) The apparatus should also preferably be simple to operate and economic to manufacture.

(5) The apparatus should, in addition, preferably be battery-operable for portable application to ambulant patients and it follows that the apparatus should be economic in power consumption.

It will be appreciated that the first two of these factors are more important clinically than the remainder, the latter being preferable from the point of view of flexibility and economy of use.

Bearing in mind the above factors and the relative importance thereof, an object of the present invention is to provide an improved syringe driving apparatus and, to this end, it is proposed that such an apparatus comprise an elongate support formed for securement therealong of the barrel of a syringe, an electric motor, a transmission assembly drivably coupled with said motor and engageable with the plunger of said syringe to move said plunger into said barrel, drive control means for repeatedly applying electrical signals at an adjustable frequency to energise said motor by each such signal to produce a predetermined incremental movement of said plunger by said transmission system, and safety control means for inhibiting said drive control means in response to energisation of said motor thereby for a predetermined continuous period of time.

Also, it is preferred that the proposed apparatus of the present invention have additional features as expressed in the appended claims, and a fuller understanding of the various features of the invention will be facilitated by consideration of one embodiment thereof.

This embodiment is illustrated in the accompanying drawings, in which:

FIG. 1 is a diagrammatic side view with a casing partially broken away to expose interior detail, and which detail is partially shown in sectioned form;

FIG. 2 is a partial cross-sectional view taken at I—I in FIG.1; and

Figure 3:
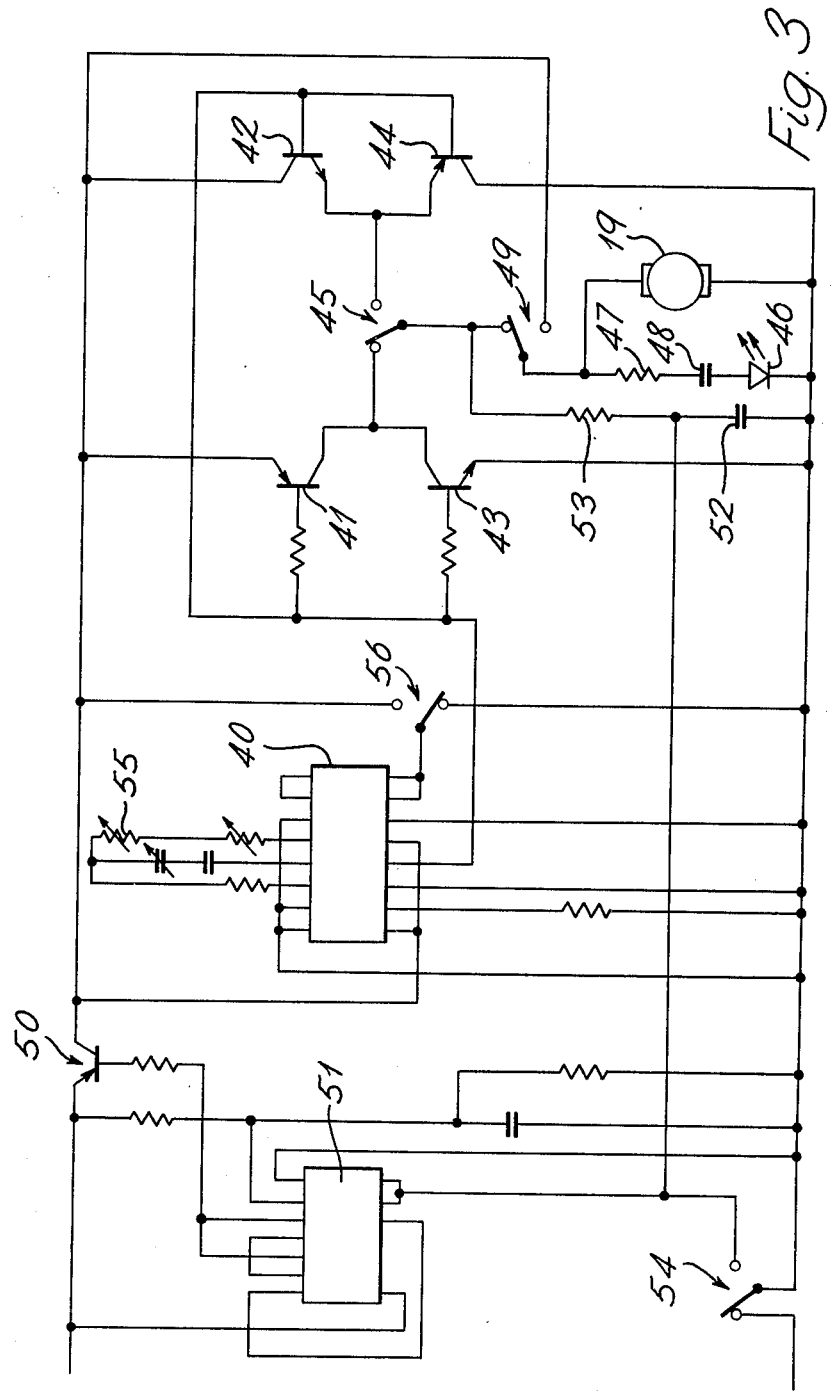
FIG. 3 is the circuit diagram.

The illustrated apparatus comprises a casing 10 which serves as a housing for some components and a chassis for others. The casing is of elongated form with laterally projecting portions 11 and 12 at its ends. These portions project in the same direction to define an elongated recess 13 therebetween, and they are of markedly different longitudinal extents with portion 11 being the longer one and representing a significant proportion of the length of the casing.

The casing structure involves two transverse members 14 and 15 of thicker material, which members respectively form the end walls of the recess 13 in the projecting portions 11 and 12. The remainder of the casing is of thinner material and involves a transverse partition 16 dividing the casing interior into two compartments 17 and 18 at respectively opposite end portions of the casing.

The compartment 17 houses a motor and reducing gear, these components being denoted generally at 19 and being mounted on the transverse member 14. The motor is of the low-inertia, permanent magnet, low-voltage type and its reducing gear is directly coupled with a lead screw 20 extending along the recess 13. The lead screw is carried at its ends in bearings 21 and 22 respectively located in the transverse members 14 and 15, the former bearing being sealed. It will be seen that the member 14 is formed as an inverted J shape to provide two longitudinally-spaced transverse portions of which the arms respectively carry the motor/gear 19 and the lead screw 20, with these components being coupled in the space between the arms. Also, in this space, a cam 23 is fixed on the lead screw and co-operates with a sprung cam follower 24.

The floor of the recess 13 serves as a slideway for a drive member 25 which is bored for free passage of the lead screw therethrough. This drive member involves an L-shaped configuration of which the base extends along the floor of the recess and around the lead screw, and the upright projects from the recess in the same direction as the casing projections 11 and 12. The upright is hollowed and transversely partially partitioned to house a half-nut 26 adjacent the lead screw, and also a rod 27 which projects away from the lead screw, through the partition, to terminate in a push-button 28 exposed at the outer end of the upright. A compression spring 29 is located around the rod 27 to act between the push-button and partition.

In operation of the apparatus as so far described, the spring 29 acts to engage the half-nut 26 with the lead screw 20, and actuation of the motor/gear 19 rotates the lead screw to drive the half-nut, and the drive member 25 therewith, towards the casing portion 11. The drive member can be returned along the lead screw by manual depression of the push-button 27 to disengage the half-nut from the lead screw.

In practical application the drive member is employed to drive, by the motor action, the plunger of a syringe. In this connection the casing portion 11 is laterally dished along the whole extent of its outermost longitudinal face to form a cradle in which the barrel of a conventional medical syringe 30 can be seated. The syringe is seated with the finger-engagement flange 30a of its barrel 30b abutting the member 14 at the adjacent end of recess 13, and the free end of the syringe plunger 30c is abutted by the carriage upright. The syringe is held in the cradle by a strap 31 secured to one side of the casing portion 11 for co-operation with a fastener (not shown) secured to the other side of such portion.

The further interior detail of the apparatus comprises a tubular battery holder 32 having a closed end secured to the casing partition 16, and an open end seated in an aperture formed in the transverse member 15. This holder is closed at its open end by a lid 33 slidably engaged with the member 15. The holder and its lid house standard cylindrical batteries 34 in serial connection between two terminals 35 and 36 in the form of bolts. One terminal bolt, 35, additionally serves to secure the closed end of the holder to the casing partition 16 and is seated in a well 37 in the inner face of such end for engagement only by a projecting pole of a battery. The other terminal bolt, 36, passes through the member 15 to engage a contact plate 38 mounted on the inner face of the lid 33 for engagement with the adjacent battery.

Electrical connections are made between the terminals 35, 36, and the motor 19 by way of a control circuit of the form shown in FIG. 3. In this figure the integrated circuit 40 comprises an R-C oscillator and a multi-stage binary divider, with a plurality of selectable stages, which delivers rectangular pulses of alternating polarity and equal mark-space ratio. These pulses are applied to four transistors 41 – 44 of which the first two connect the motor for driving energisation and the other two connect the motor for electromagnetic braking. These connections all involve a microswitch 45 which is operated by the cam 23, by way of the cam follower 24.

The cam is of regular multi-lobed form and changes over the microswitch each $\frac{1}{2}$n of a revolution of the lead screw, where n is the number of lobes on the cam. The operation of the motor is such that, with the microswitch operated to the position illustrated in FIG. 3, a negative pulse opens transistor 41 to energise the motor and drive the lead-screw until, after $\frac{1}{2}$n of a revolution, the microswitch is changed over. This change-over terminates the motor drive action and connects transistor 44, which is also opened by the aforementioned negative pulse, to allow electromagnetic braking to occur. When the negative pulse terminates and a positive pulse commences transistors 41 and 44 are closed, transistors 42 and 43 are opened, and the motor is energised through transistor 42 and the microswitch until the microswitch is changed over after a further $\frac{1}{2}$n revolution of the lead screw, whereafter an electromagnetic braking connection is made through transistor 43.

A light-emitting diode 46 is connected across the motor, through a resistor 47 and a capacitor 48, and flashes momentarily each time the motor is pulsed for drive action. The resultant repeated flashing accordingly indicates normal operation.

In addition the motor can be tested by a push-button switch 49 provided for this purpose. The switch 49 serves, when operated, to override the pulsed control of the motor by disconnecting the motor from the microswitch and associated transistors, and instead connects the motor directly to the battery supply by way of a transistor 50.

The circuit of FIG. 3 also acts to prevent continuous running of the motor in the event that a fault occurs. This action is effected by the provision of a latch 51 which is activated by way of a capacitor 52 and resistor 53. This capacitor is charged by way of its resistor and the microswitch when the motor is activated, and with normal intermittent activation of the motor the capacitor does not charge sufficiently to operate the latch, even when the motor is pulsed at the highest available frequency. However, if, because of a fault, the motor is energised continuously for more than a predetermined period, the latch is operated to switch off the transistor 50 and thereby disconnect all facilities except the latch itself from the power supply. The relevant charging period for the capacitor 52 after which the latch operates is suitably chosen to be about four times the normal motor energisation pulse period.

Resetting of the latch involves momentary operation of a push button switch 54. This operation disconnects the battery supply from the latch and thereby allows the latter to reset, while at the same time discharging the capacitor 52. The transistor 50 is then closed again upon release of the reset switch.

Remaining features of FIG. 3 concern variation of the pulse output frequency of the integrated circuit 40 in order to vary the overall rate at which the carriageway 25 is driven along the shaft 21. One such feature comprises a potentiometer 55 which varies the frequency of the oscillator component of circuit 40, and another such feature comprises a switch 56 which changes over the output of the divider component of circuit 40 between two different stages thereof. Thus two ranges of pulse frequency variation are provided by adjustment of the potentiometer 55 in association with respective settings for the switch 56, and it is clearly preferable that these ranges be substantially continuous or in overlapping relationship to a minor degree. In practice for this last purpose the variation factor effected by the switch should not exceed the maximum possible with the potentiometer and, as an example, a current version of the illustrated embodiment provides a 12:1 frequency range from the oscillator and an 8:1 shift in the divider output giving an overall frequency range of 96:1. This last range takes account of the differing maximum strokes between standard syringes of differing capacity, namely, 3 cm for a 2 ml syringe and 5 cm for a 10 ml syringe, and allows for variation of the period of administration of such quantities to be varied widely, namely, from $\frac{1}{2}$ hour to 24 hours.

Selection of a desired administration period for a given size of syringe can be effected by setting a rotary scale member 39 mounted on the casing 10 and operably coupled with the potentiometer 55. The switch 56 can be arranged for automatic operation to one range setting or the other by movement of the scale member over appropriate portions of its range, or the switch may be independently accessible from without the casing. In the present embodiment it is preferred to employ automatic operation of the switch 56, with the scale member 39 having two sets of range markings respectively exposable through arcuate windows only when the switch 56 is appropriately set by rotation of the scale member.

Considering now the advantageous features of the invention as represented by the illustrated embodiment: these meet the desired factors enumerated above.

The embodiment takes account of hazardous malfunctions by way of the latch 51. This latch serves primarily to guard against the possibility of continuous running of the motor, and in this event the latch operates to stop the syringe movement. In addition, the latch is operated if the motor is slowed down or stalled by an overload or when the drive member 25 has been driven to the end of the lead screw 20. A further indication of malfunction is given by the LED 46.

The embodiment is reliable in terms of administered dosage by virtue of the cam-operated microswitch which terminates each drive pulse to the motor with reference to a predetermined point of lead screw rotation. Any alternative arrangement relying wholly on electronically-determined pulse periods may be subject to accumulative error in dosage administration rate by virtue of inertia in the motor. In the present case, the provision of electromagnetic braking also reduces such errors and ensures that the drive action terminates within the relevant partial revolution of the lead screw.

The embodiment is capable of administering dosage within a wide range as has been discussed above.

The embodiment is simple to operate. The condition of the batteries is readily established by operation of the push-button switch 49 since sufficient power is available if the motor runs continuously. Location of the syringe and appropriate positioning of the carriage 29 relative to the syringe plunger is easily affected by the use of the syringe strap 31 and carriage push-button 28. The remaining operation requirement is appropriate setting of the scale member 39. At present the two sets of scale markings respectively denote minutes and hours to represent the time taken for the carriage to be driven 1 cm. Thus, it is only necessary for a user to measure the required distance of plunger travel within the syringe and, with a knowledge of the required administration period, calculate the necessary setting for the scale member. Simple instructions for this operating procedure can be provided on the casing 10, as can ruler markings for measuring the relevant plunger distance before mounting the syringe.

It will be seen that the motor, reduction gear, circuits, and batteries are all protected within the casing, against contamination by liquid. The lead screw and drive member are, in contrast, fully exposed but can be of materials which are not subject to contamination difficulties, for example, stainless steel and plastics materials.

Manufacture of the embodiment is at least comparable in economy with previously proposed devices intended to serve a similar purpose.

Clearly the embodiment is portable by virtue of its battery operation and the embodiment is economic in power consumption by virtue of the choice of motor speed and pulse frequency. In addition, it will be noted that the latch 51 operates to disconnect the power supply in circumstances when power would otherwise be wasted, in particular, when the carriage reaches the end of the lead screw. In practice the present embodiment can operate for 300–400 "full length deliveries" with one set of three 1.3 v mercury cell batteries. Also, it will be noted that the embodiment requires no ON/OFF switch.

One final comment regarding the portability of the embodiment, for use by ambulatory patients, concerns the manner of carrying the apparatus. Tests with the present embodiment indicate that a particularly convenient mode of carriage is effected by the use of a pouch having straps to form a carrier which is worn in the manner of a pistol shoulder holster.

I claim:

1. Syringe driving apparatus comprising an elongate support formed for securement therealong of the barrel of a syringe, an electric motor, a transmission assembly drivably coupled with said motor and engageable with the plunger of said syringe to move said plunger into said barrel, drive control means for repeatedly applying uniform electrical signals at an adjustable frequency to energise said motor by each such signal to produce a predetermined incremental movement of said plunger by said transmission system, and safety control means for inhibiting said drive control means in response to energisation of said motor thereby for a predetermined continuous period of time greater than the duration of each of said drive control signals during normal operation of the apparatus.

2. Apparatus according to claim 1 wherein said safety control means comprises a capacitor connected to said drive control means to be charged by each of said signals and to be discharged in each interval between said signals, and a latch operable to inhibit said drive control means in response to charging of said capacitor to a predetermined level.

3. Apparatus according to claim 1 wherein said transmission assembly includes a rotary switch-operating member cyclically driven by said motor in synchronism with successive ones of said incremental movements, and said drive control means includes a variable-frequency pulse generator providing a pulse train output of constant mark-space ratio for application to energise said motor, and a switch operable by said member to terminate application of successive pulses of said train to said motor.

4. Apparatus according to claim 3 wherein said drive control means comprises two circuits each activated by successive pulses of said train of common polarity respectively to energise said motor and to allow regenerative braking of said motor, and said switch is operable to complete and open said two circuits in alternating and mutually opposite manner.

5. Apparatus according to claim 3 wherein said generator provides a train of pulses of successively alternating polarity, said drive control means comprises two parallel circuits respectively responsive to said pulses of opposite polarity to energise said motor, and said switch is operable to complete and open said parallel circuits in alternating and mutually opposite manner.

6. Apparatus according to claim 5 wherein said drive control means includes two further circuits respectively responsive to said pulses of opposite polarity to allow regenerative braking of said motor, and said switch is operable to complete and open said two further circuits in opposite manner relative to said parallel circuits.

7. Apparatus according to claim 3 wherein said pulse generator includes a variable frequency oscillator applied to a multi-stage binary frequency divider, and said drive control means includes a further switch operable to change the output of said generator between two different stages of said divider, the maximum ratio of frequency variation provided for said generator by said divider stage switch being no greater than that provided by variation of said oscillator.

8. Apparatus according to claim 1 wherein said motor is of low-inertia, permanent magnet, low voltage type, and said support comprises a holder for batteries to energise said motor and said drive control means.

9. Apparatus according to claim 1 wherein: said support is in the form of an elongate casing having lateral projections in a common direction from its opposite end portions to define an exposed elongate recess therein, one of said projections defining a cradle to receive said syringe barrel and having a strap to secure said syringe in said cradle; and said transmission assembly comprises a lead screw drivably connected with said motor, disposed longitudinally along said recess, and supported by bearings carried in said projections, and a plunger drive member including a nut threadably engaging said lead screw.

10. Apparatus according to claim 9 wherein said plunger drive member comprises an elongate first body portion freely longitudinally embracing said lead screw and slidably engaged with said casing, a second body portion extending transversely from said first portion to engage said syringe plunger, and a half-nut housed in said first body portion and releasably sprung into threaded engagement with said lead screw.

* * * * *